United States Patent
Gaffney et al.

(10) Patent No.: US 12,186,518 B2
(45) Date of Patent: Jan. 7, 2025

(54) FLUID CONNECTOR SYSTEM

(71) Applicant: CareFusion 303, Inc., San Diego, CA (US)

(72) Inventors: Leah Paige Gaffney, Orange, CA (US); Abin Austin, Thrissur (IN); Mohammed Mehtab Khan, Bengaluru (IN); Aman Desai, Bengaluru (IN); Narsi Reddy Sanikommu, Kanigiri (IN); Anuj Niranjanchavan, Pune (IN); Sachin Gawali, Pune (IN)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/306,529

(22) Filed: Apr. 25, 2023

(65) Prior Publication Data

US 2024/0358988 A1  Oct. 31, 2024

(51) Int. Cl.
*A61M 39/10* (2006.01)
*A61M 39/26* (2006.01)
(Continued)

(52) U.S. Cl.
CPC .............. *A61M 39/10* (2013.01); *F16L 37/34* (2013.01); *A61M 2039/1027* (2013.01);
(Continued)

(58) Field of Classification Search
CPC .......... A61M 39/10; A61M 2039/1027; A61M 2039/1061; A61M 39/26;
(Continued)

(56) References Cited

U.S. PATENT DOCUMENTS 5,713,856 A  2/1998  Eggers et al.
5,820,614 A * 10/1998  Erskine ............... F16L 55/1007
                                                        604/905
(Continued)

FOREIGN PATENT DOCUMENTS

EP  1678070 A2  7/2006
EP  1517723 B1  1/2007
(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.
(Continued)

*Primary Examiner* — David Colon-Morales
(74) *Attorney, Agent, or Firm* — Morgan, Lewis & Bockius LLP

(57) ABSTRACT

Fluid connector systems including first and second connector portions couplable together to form a fluid pathway therethrough and can resist separation or permit separation as desired. A connector portion can include a connector housing and a cover portion. The connector housing includes a connector body and an engagement portion. The connector body defines a tubing opening and a mating opening. The connector body defines a flow path between the tubing opening and the mating opening. The engagement portion at least partially surrounds the connector body. The engagement portion defines an engagement lip extending radially toward the connector body and is configured to releasably engage the connector housing. The flow path includes at least one portion that is normal to the engagement portion. Fluid flow through the flow path exerts a normal force on the
(Continued)

connector housing and prevent release of the connector housing with the mating connector portion.

20 Claims, 7 Drawing Sheets

(51) Int. Cl.
  *F16L 37/34* (2006.01)
  *F16L 37/46* (2006.01)
(52) U.S. Cl.
  CPC .............. *A61M 2039/1061* (2013.01); *A61M 2039/267* (2013.01); *F16L 37/46* (2013.01)
(58) Field of Classification Search
  CPC ........... A61M 2039/267; F16L 55/1015; F16L 37/46; F16L 37/367; F16L 37/34; F16L 37/413
  See application file for complete search history.

(56) References Cited

U.S. PATENT DOCUMENTS

| | | | |
|---|---|---|---|
| 6,874,522 B2 | 4/2005 | Anderson et al. | |
| 7,004,934 B2 | 2/2006 | Vaillancourt | |
| 7,040,598 B2 | 5/2006 | Raybuck | |
| 7,044,441 B2 * | 5/2006 | Doyle | A61M 39/26 251/149.6 |
| 7,153,296 B2 | 12/2006 | Mitchell | |
| 7,350,764 B2 | 4/2008 | Raybuck | |
| 7,396,051 B2 | 7/2008 | Baldwin et al. | |
| 7,763,013 B2 | 7/2010 | Baldwin et al. | |
| 7,766,394 B2 | 8/2010 | Sage et al. | |
| 7,794,675 B2 | 9/2010 | Lynn | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,918,243 B2 | 4/2011 | Diodati et al. | |
| 7,998,134 B2 | 8/2011 | Fangrow et al. | |
| 8,123,738 B2 | 2/2012 | Vaillancourt | |
| 8,142,418 B2 | 3/2012 | McMichael et al. | |
| 8,211,069 B2 | 7/2012 | Fangrow, Jr. | |
| 8,262,628 B2 | 9/2012 | Fangrow, Jr. | |
| 8,361,408 B2 | 1/2013 | Lynn | |
| 8,480,968 B2 | 7/2013 | Lynn | |
| 8,777,908 B2 | 7/2014 | Fangrow, Jr. | |
| 8,777,909 B2 | 7/2014 | Fangrow, Jr. | |
| 8,795,256 B1 * | 8/2014 | Smith | A61M 39/26 604/249 |
| 8,888,758 B2 | 11/2014 | Mansour | |
| 8,899,267 B2 | 12/2014 | Diodati et al. | |
| 8,910,919 B2 | 12/2014 | Bonnal et al. | |
| 8,945,091 B2 * | 2/2015 | Williams | A61M 39/10 285/305 |
| 8,974,425 B2 | 3/2015 | Tachizaki et al. | |
| 8,974,437 B2 | 3/2015 | Williams et al. | |
| 9,114,242 B2 | 8/2015 | Fangrow et al. | |
| 9,126,028 B2 | 9/2015 | Fangrow et al. | |
| 9,126,029 B2 | 9/2015 | Fangrow et al. | |
| 9,192,753 B2 | 11/2015 | Lopez et al. | |
| 9,234,616 B2 | 1/2016 | Carrez et al. | |
| 9,358,379 B2 | 6/2016 | Fangrow, Jr. | |
| 9,433,769 B2 | 9/2016 | Bayly | |
| 9,468,749 B2 | 10/2016 | Mansour et al. | |
| 9,492,649 B2 | 11/2016 | Carrez et al. | |
| 9,636,492 B2 | 5/2017 | Fangrow, Jr. | |
| 9,724,504 B2 | 8/2017 | Fangrow, Jr. et al. | |
| 9,724,505 B2 | 8/2017 | Williams et al. | |
| 9,861,805 B2 | 1/2018 | Dennis et al. | |
| 9,933,094 B2 * | 4/2018 | Fangrow | A61M 39/18 |
| 9,974,939 B2 | 5/2018 | Fangrow, Jr. | |
| 9,974,940 B2 | 5/2018 | Fangrow, Jr. | |
| 10,029,086 B2 | 7/2018 | Nowak et al. | |
| 10,156,306 B2 | 12/2018 | Fangrow | |
| 10,173,045 B2 | 1/2019 | Mansour | |
| 10,179,203 B1 | 1/2019 | Huslage et al. | |
| 10,315,025 B2 | 6/2019 | Phillips et al. | |
| 10,398,887 B2 | 9/2019 | Fangrow, Jr. et al. | |
| 10,441,507 B2 | 10/2019 | Sanders | |
| 10,518,078 B2 | 12/2019 | Stjernberg Bejhed et al. | |
| 10,569,073 B2 * | 2/2020 | Hallisey | A61M 39/26 |
| 10,625,068 B2 * | 4/2020 | Leuthardt | A61M 39/10 |
| 10,655,768 B2 * | 5/2020 | Jones | A61M 39/24 |
| 10,697,570 B2 | 6/2020 | Fangrow | |
| 10,744,315 B2 | 8/2020 | Sanders | |
| 10,842,982 B2 | 11/2020 | Fangrow, Jr. | |
| 10,857,346 B2 | 12/2020 | Dennis et al. | |
| 10,864,362 B2 * | 12/2020 | Jones | A61M 5/16813 |
| 10,881,847 B2 | 1/2021 | Lynn | |
| 11,168,818 B2 | 11/2021 | Fangrow | |
| 11,207,514 B2 | 12/2021 | Kakinoki | |
| 11,235,135 B2 | 2/2022 | Tsai | |
| 11,273,297 B2 | 3/2022 | Kakinoki | |
| 11,484,471 B2 | 11/2022 | Sanders | |
| 11,491,084 B2 | 11/2022 | Ueda et al. | |
| 11,708,926 B2 * | 7/2023 | Bryan | F16L 37/32 251/149.6 |
| 2004/0215158 A1 | 10/2004 | Anderson | |
| 2005/0090805 A1 | 4/2005 | Shaw et al. | |
| 2006/0129109 A1 * | 6/2006 | Shaw | A61M 39/26 604/246 |
| 2007/0088292 A1 | 4/2007 | Fangrow, Jr. | |
| 2007/0088293 A1 | 4/2007 | Fangrow, Jr. | |
| 2007/0088294 A1 | 4/2007 | Fangrow, Jr. | |
| 2007/0225635 A1 | 9/2007 | Lynn | |
| 2008/0039803 A1 | 2/2008 | Lynn | |
| 2011/0106046 A1 | 5/2011 | Hiranuma | |
| 2011/0257607 A1 | 10/2011 | Whitley | |
| 2014/0175314 A1 * | 6/2014 | Bondo | F16L 37/34 251/149.6 |
| 2014/0249487 A1 | 9/2014 | Lynn | |
| 2014/0330254 A1 | 11/2014 | Rosenberger et al. | |
| 2015/0297830 A1 | 10/2015 | Okiyama | |
| 2016/0000363 A1 | 1/2016 | Jones et al. | |
| 2018/0200147 A1 | 7/2018 | Sanders | |
| 2019/0184152 A1 | 6/2019 | Kakinoki | |
| 2019/0282797 A1 | 9/2019 | Tsai | |
| 2020/0113784 A1 | 4/2020 | Lopez et al. | |
| 2020/0179672 A1 | 6/2020 | Kakinoki | |
| 2020/0215319 A1 | 7/2020 | Fangrow, Jr. et al. | |
| 2020/0284385 A1 | 9/2020 | Fangrow | |
| 2020/0323734 A1 | 10/2020 | Ueda et al. | |
| 2020/0338331 A1 | 10/2020 | Sanders | |
| 2021/0069484 A1 | 3/2021 | Tsai | |
| 2021/0077803 A1 | 3/2021 | Lynn | |
| 2021/0252267 A1 | 8/2021 | Fangrow, Jr. | |
| 2021/0388926 A1 | 12/2021 | Martin et al. | |
| 2021/0393938 A1 | 12/2021 | Lynn et al. | |
| 2022/0260189 A1 | 8/2022 | Deuse | |
| 2022/0282814 A1 | 9/2022 | Fangrow | |
| 2023/0086505 A1 * | 3/2023 | Fischer | A61M 39/26 285/70 |

FOREIGN PATENT DOCUMENTS

| | | |
|---|---|---|
| EP | 1622675 B1 | 8/2009 |
| EP | 2144634 A1 | 1/2010 |
| EP | 2298407 A1 | 3/2011 |
| EP | 2694132 A1 | 2/2014 |
| EP | 2562456 B1 | 6/2014 |
| EP | 2782633 A1 | 10/2014 |
| EP | 1842002 B1 | 4/2015 |
| EP | 2736582 B1 | 5/2015 |
| EP | 2089094 B1 | 1/2016 |
| EP | 2219721 B1 | 12/2017 |
| EP | 2753396 B1 | 12/2017 |
| EP | 2736584 B1 | 4/2018 |
| EP | 3305361 A1 | 4/2018 |
| EP | 2271398 B1 | 11/2018 |
| EP | 2480281 B1 | 11/2018 |
| EP | 2790750 B1 | 11/2018 |
| EP | 2331191 B1 | 3/2019 |

(56) References Cited

FOREIGN PATENT DOCUMENTS

| | | |
|---|---|---|
| EP | 3079756 B1 | 3/2019 |
| EP | 2121114 B1 | 5/2019 |
| EP | 2719419 B1 | 5/2019 |
| EP | 2956204 B1 | 8/2019 |
| EP | 3421077 B1 | 8/2019 |
| EP | 3530313 A1 | 8/2019 |
| EP | 3538201 A1 | 9/2019 |
| EP | 3570807 A1 | 11/2019 |
| EP | 3570809 A1 | 11/2019 |
| EP | 2536463 B1 | 4/2020 |
| EP | 3381505 B1 | 5/2020 |
| EP | 3538201 B1 | 5/2020 |
| EP | 1904152 B1 | 12/2020 |
| EP | 2150307 B1 | 12/2020 |
| EP | 3313490 B1 | 1/2021 |
| EP | 3760275 A1 | 1/2021 |
| EP | 3851155 A1 | 7/2021 |
| EP | 3517164 B1 | 9/2021 |
| EP | 3954355 A1 | 2/2022 |
| EP | 3960229 A1 | 3/2022 |
| EP | 3973044 A1 | 3/2022 |
| EP | 3305361 B1 | 5/2022 |
| EP | 3134052 B1 | 8/2022 |
| EP | 3530313 B1 | 8/2022 |
| WO | WO-2006043883 A1 | 4/2006 |
| WO | WO-2014041581 A1 * | 3/2014 ............ A61M 39/26 |
| WO | WO-2021099437 A1 | 5/2021 |
| WO | WO-2021180675 A1 | 9/2021 |
| WO | WO-2021252197 A1 | 12/2021 |
| WO | WO-2022042956 A1 | 3/2022 |
| WO | WO-2022149339 A1 | 7/2022 |
| WO | WO-2022207560 A1 | 10/2022 |

OTHER PUBLICATIONS

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

Ivteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 May 2021 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

International Search Report and Written Opinion for Application No. PCT/US2024/025222, dated Aug. 1, 2024, 12 pages.

* cited by examiner

FLUID CONNECTOR SYSTEM

BACKGROUND

The present disclosure relates generally to medical fluid connectors and, more particularly, to fluid connector systems having valve assemblies that can be coupled together to form a fluid pathway.

Medical connections are widely used in fluid delivery systems such as those used in connection with intravenous (IV) fluid lines, blood access, hemodialysis, peritoneal dialysis, enteral feeding, drug vial access, and other procedures.

In some instances, the medical connection can become dislodged or disconnected in an unintended manner. For example, medical tubing of an IV set that is coupled to a catheter can become dislodged when an unintended or unexpected forces is exerted upon the catheter, which may exceed the design limitations of the catheter securement method. An unintended or unexpected force can be applied to the tubing and/or catheter when the patient moves or rolls over within a bed, or when the tubing or another portion of an intravenous set become caught on a portion of the bed, such as the railing, or when a patient is panicking, disoriented, or fidgeting to such an extent that the medical tubing is unintentionally or intentionally pulled away from the patient or away from the medical equipment coupled to the tubing.

In some applications, high pressure medical fluids (up to or in excess of 325 psi) can be utilized in certain medical infusions. In certain applications, a medical connection can become disconnected when a high pressure medical fluid is passed through the connection.

SUMMARY

In accordance with at least some embodiments disclosed herein is the realization that unintended dislodgement or disconnection of a medical connection, such as a medical fluid line, can result in injury to a patient or a caregiver, such as by depriving the patient of a medicament, increasing the potential for infection to the patient, and exposing the caregiver to harmful medicaments.

Accordingly, aspects of the present disclosure provide a connector comprising a first connector portion comprising: a connector housing comprising: a connector body defining a tubing opening and a mating opening, wherein the connector body defines a flow path between the tubing opening and the mating opening; and an engagement portion at least partially surrounding the connector body, the engagement portion defining an engagement lip extending radially toward the connector body, wherein the engagement lip is configured to releasably engage the connector housing with a mating connector portion, wherein the flow path comprises at least one portion that is normal to the engagement portion, wherein fluid flow through the flow path exerts a normal force on the connector housing and prevent release of the connector housing with the mating connector portion.

In some instances, the present disclosure provides a connector comprising a first connector portion defining a tubing opening and a mating opening, wherein the first connector portion defines a flow path between the tubing opening and the mating opening; and a second connector portion comprising defining a second tubing opening and a second mating opening, wherein the second connector portion defines a second flow path between the second mating opening and the tubing opening, wherein the mating opening of the first connector portion and the second mating opening of the second connector portion are in fluid communication when the first connector portion and the second connector portion are in engagement, wherein the flow path or the second flow path comprises at least one portion that is normal to an overlapping portion of the first connector portion and the second connector portion, wherein fluid flow through the flow path or the second flow path exerts a normal force on the overlapping portion of the first connector portion and the second connector portion and prevent release of the first connector portion with the second connector portion.

Accordingly, the present application addresses several operational challenges encountered in prior fluid connections and provides numerous improvements that enable the user to increase safety and efficacy, while more easily and precisely providing fluid connections.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
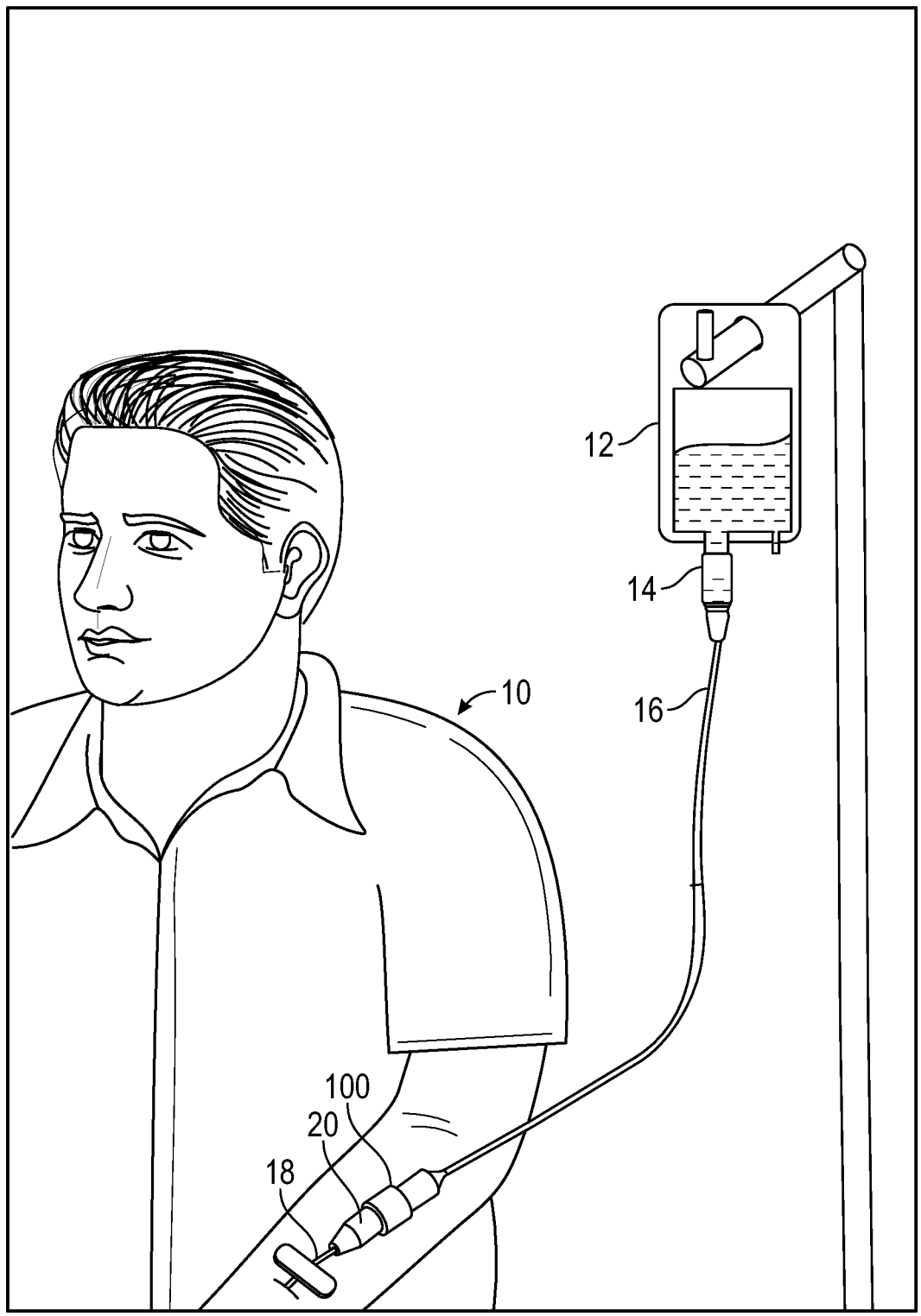
FIG. 1 illustrates a fluid connector in use with an IV set coupled to a patient, in accordance with aspects of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of a fluid connector system. The fluid connector system can provide for efficient and safe maintenance of fluid connections, such as the connections used for transferring medical fluids toward or away from a patient. The fluid connector system can maintain a fluid pathway by resisting unintended disconnection when a pulling or tension force is applied to the fluid connector system, such as when a patient moves or when the medical tubing is pulled away from the patient.

The fluid connector system can also prevent injury to a patient or a caregiver by permitting disconnection or separation between portions of the connector system when a pulling or tension force exceeds a threshold. The fluid connector system can also prevent injury to a patient or a caregiver by obstructing the fluid pathway when disconnection or separation between portions of the connector system occurs. Further, the fluid connector system can provide for efficient and safe reestablishment of the fluid pathway, by permitting reassembly of portions of the system after a disconnection or separation occurs. Advantageously, the fluid connectors described herein can prevent blood loss, IV fluid loss, infection, and/or delays in medication delivery. In some applications, the design of the fluid connectors can facilitate effective cleaning and sanitization of the components.

Further, in some applications, the fluid connector system can resist unintended disconnection during certain events or applications, and selectively but allow for disconnection or separation between portions of the connector system when a pulling or tension force exceeds a threshold. For example, a fluid connector system can be configured to resist disconnection or separation during high pressure infusion (fluid pressures up to or in excess of 325 psi) or during other clinical operations that may cause the fluid connector system to unintentionally separate. The fluid connector system may also selectively allow for disconnection or separation between portions of the connector system when a pulling or tension force exceeds a threshold.

Referring now to the figures, FIG. 1 illustrates an example of a fluid connector 100 in use in accordance with aspects of the present disclosure. The connector system 100 is coupled with tubing of an IV set, which is being used to direct a fluid to a patient 10. The IV set can include a medicament bag 12, a drip chamber 14, tubing 16, and an IV catheter 18.

The connector system 100 fluidly connects the tubing 16 to the IV catheter 18. Although the connector system 100 is illustrated being coupled along a fluid pathway of an IV set, between a medicament bag 12 and a patient 10, it should be understood that the connector system 100 can be connected within other fluid pathways, such as between a patient and an IV pump or between a patient and a dialysis machine. The connector system 100 can also be connected along another portion of a fluid pathway. For example, the connector system 100 can be connected along a proximal portion of the fluid pathway, such as being connected between the tubing 16 and the medicament bag 12 or other fluid therapy device. In another example, any of the first and second portions of the fluid connector 100 can be directly coupled to another fluid delivery devices, such as the catheter or a medicament bag.

Figure 2:
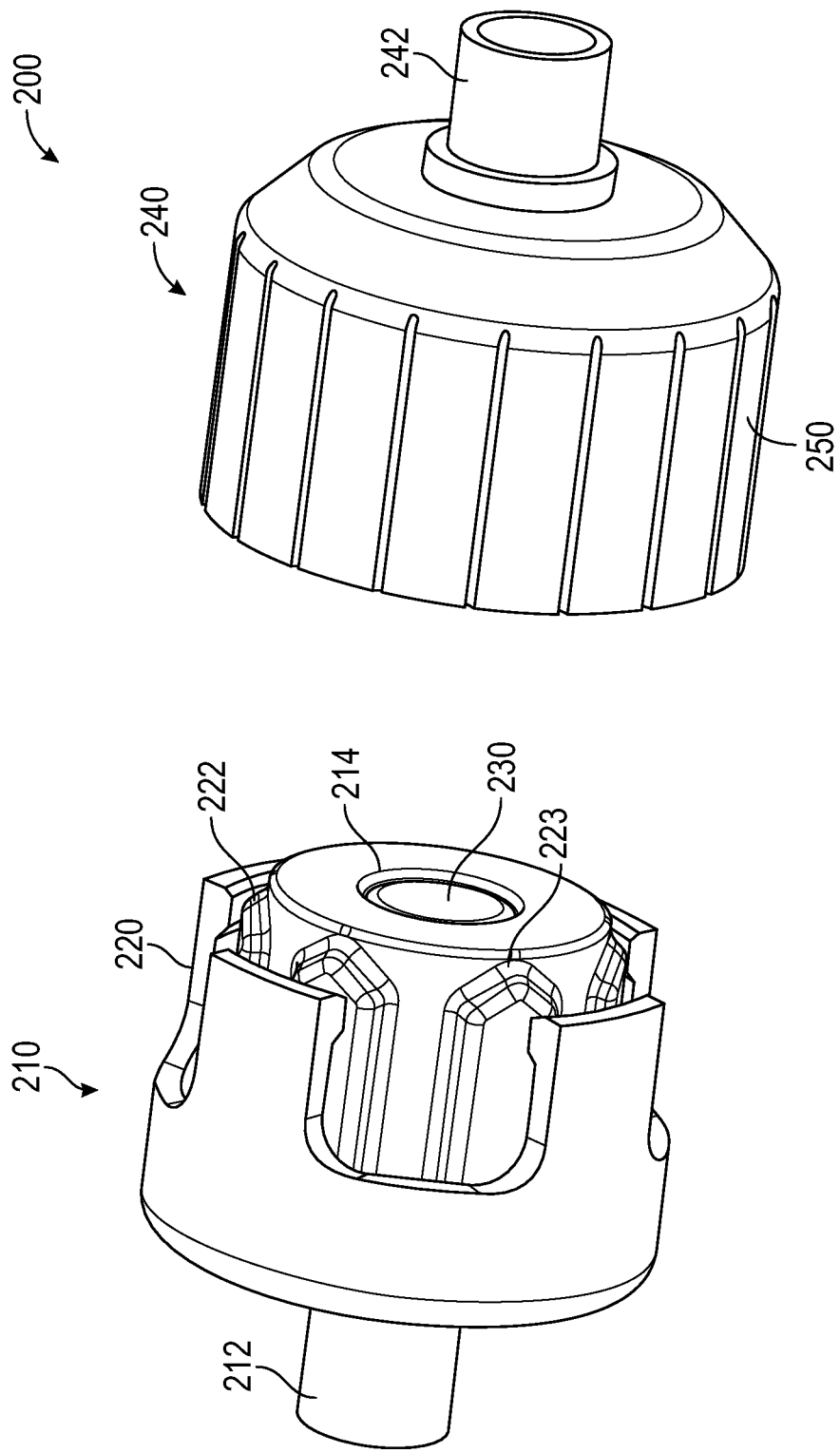
FIG. 2 illustrates a perspective view of a separated fluid connector, in accordance with aspects of the present disclosure.
Figure 3:
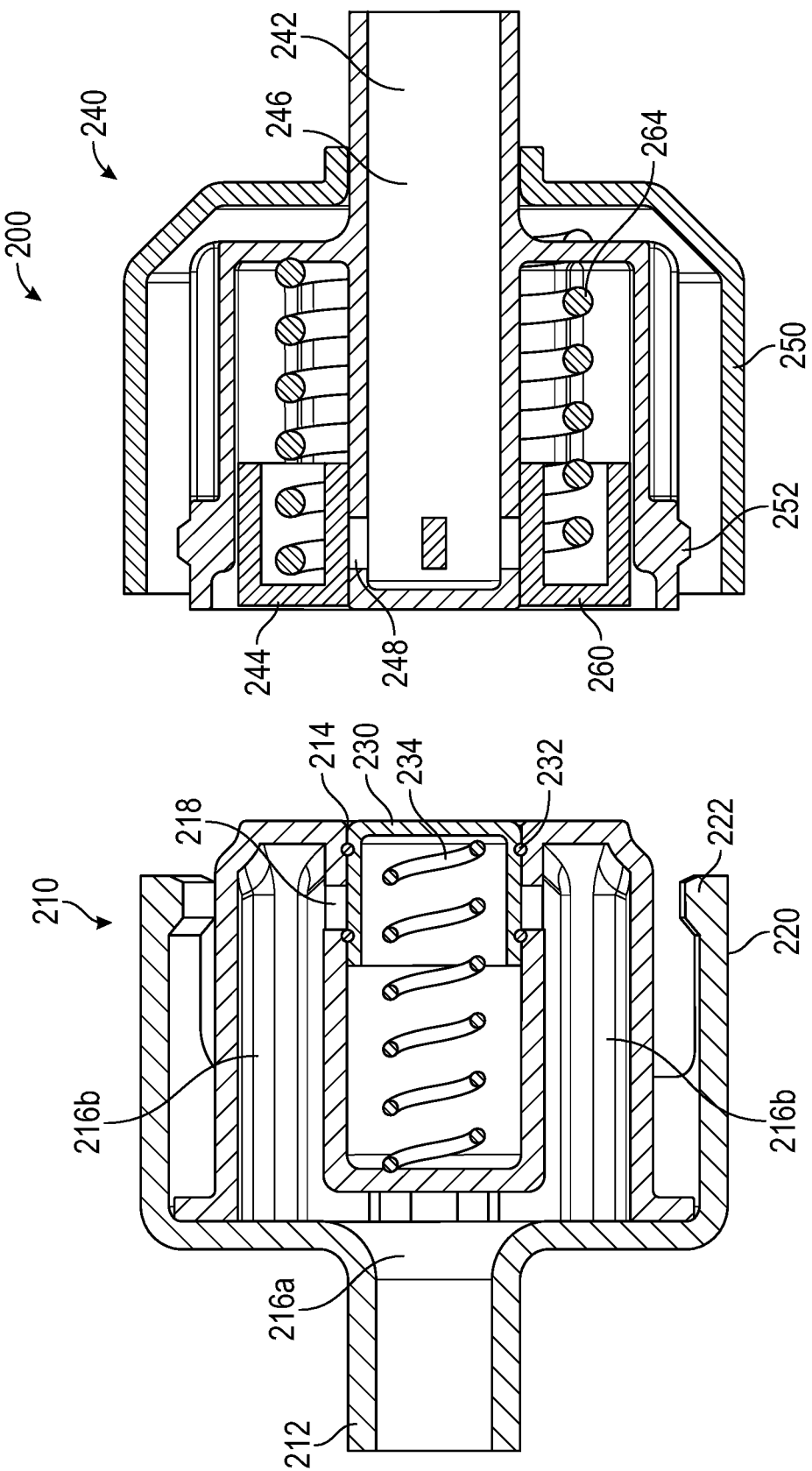
FIG. 3 illustrates a cross-sectional view of a separated fluid connector of FIG. 2, in accordance with aspects of the present disclosure.
Figure 4:
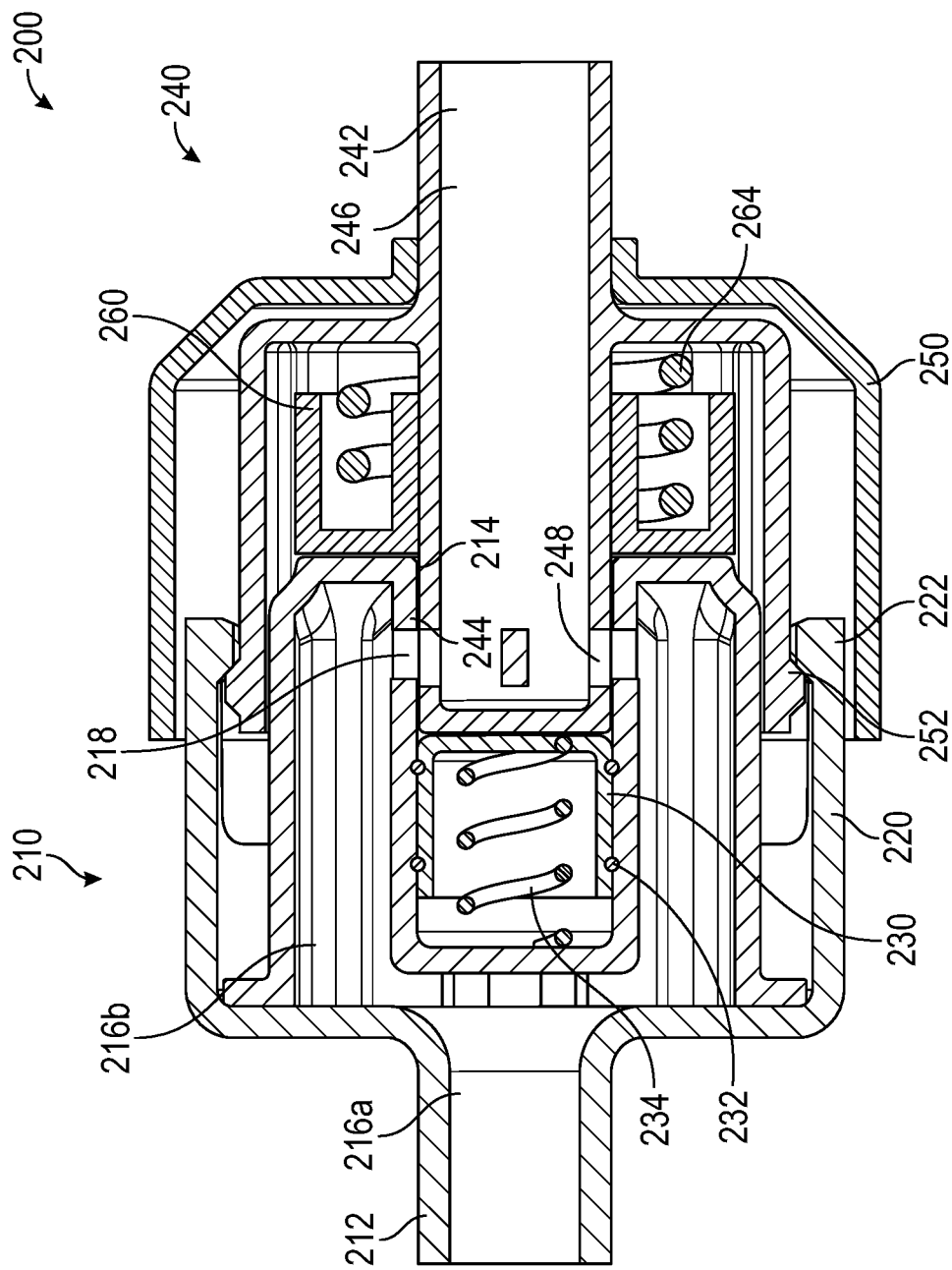
FIG. 4 illustrates a cross-sectional view of a connected fluid connector of FIG. 2, in accordance with aspects of the present disclosure.

FIG. 2 illustrates a perspective view of a separated fluid connector 200, in accordance with aspects of the present disclosure. FIG. 3 illustrates a cross-sectional view of a separated fluid connector 200 of FIG. 2, in accordance with aspects of the present disclosure. FIG. 4 illustrates a cross-sectional view of a connected fluid connector 200 of FIG. 2, in accordance with aspects of the present disclosure. With reference to FIGS. 2-4, the fluid connector 200 provides a fluid pathway to a patient while allowing for selectable a "fusible link" or quick disconnect, allowing for a controlled disconnection of the fluid connector 200 if excess force is applied and allowing for a maintained connection during high pressure infusions or other procedures. As described herein, the fluid connector 200 can allow for controlled disconnection at a predetermined level of force to prevent a catheter from being inadvertently removed from the patient or prevent inadvertent disconnection during high pressure infusion procedures.

As illustrated, the fluid connector 200 provides a flow path or fluid pathway from one end of the fluid connector 200 to the opposite end of the fluid connector 200. As illustrated, the fluid connector 200 includes a first connector portion 210 and a second connector portion 240 that are coupled together to form a fluid pathway.

In the depicted example, the first connector portion 210 permits fluid flow to and from the patient or any other portion of the IV set. In the depicted example, the first connector portion 210 includes a bond pocket or end portion 212 to be connected to mating tubing or luer connector. In some embodiments, tubing can be adhered to the first connector portion 210 at the bond pocket or end portion 212. As illustrated, a mating tubing or luer connector can be in fluid communication with the flow path 216a. In some embodiments, the flow path 216a can be in fluid communication with the annular flow path 216b defined in the body of the first connector portion 210. Therefore, fluid can pass to and from the fluid connector 200 through the mating luer connector via the flow path 216a, 216b defined in the first connector portion 210.

Further, the second connector portion 240 permits fluid flow to and from a fluid source or any other portion of the IV set. In the depicted example, the second connector portion 240 can be connected to a fluid source or other portion of the IV set. In the depicted example, the second connector portion 240 includes a bond pocket or end portion 242 to be connected to mating tubing or luer connector. In some embodiments, tubing can be adhered to the second connector portion 240 at the bond pocket or end portion 242. As illustrated, a mating tubing or luer connector can be in fluid communication with the flow path 246. Fluid can pass to and from the fluid connector 200 through the second mating luer connector via the flow path 246 defined in the second connector portion 240.

During operation, the first connector portion 210 and the second connector portion 240 can be coupled together to permit flow between the first connector portion 210 and the second connector portion 240. In the depicted example, the first connector portion 210 can define a mating opening 218 in fluid communication with the annular flow path 216b. As described herein, the flow path 216b can be in fluid communication with the flow path 216a to allow fluid communication with the tubing or other IV set component coupled to the end portion 212 of the first connector portion 210. Similarly, the second connector portion 240 can define a mating opening 248 in fluid communication with the flow path 246, and the tubing or other IV set component coupled to the end portion 242 of the second connector portion 240. As the first connector portion 210 and the second connector portion 240 are coupled together, fluid can flow between the mating opening 218 of the first connector portion 210 and the mating opening 248 of the second connector portion 240, allowing flow between the first connector portion 210 and the second connector portion 240.

In some embodiments, the first connector portion 210 can include one or more alignment features 223 to align features of the second connector portion 240 with the first connector portion 210 to facilitate physical coupling of the first connector portion 210 and the second connector portion 240 and facilitate fluid communication therebetween. In some embodiments, the alignment features 223 can include radial protrusions extending from the body of the first connector portion 210.

In the depicted example, the first connector portion 210 and the second connector portion 240 each include a valve member 230, 260 respectively to control flow through the connector 200. In particular, the valve members 230, 260 allow for fluid to flow between the first connector portion 210 and the second connector portion 240 when the first connector portion 210 and the second connector portion 240 are connected and prevent fluid flow when the first connector portion 210 and the second connector portion 240 are disconnected.

In the depicted example, the first valve member 230 is movable within a valve cavity 214 to permit flow through the mating opening 218 and to prevent flow through the mating opening 218. In an occluding position, the first valve member 230 can block, occlude, or seal against the mating opening 218 to prevent flow through the mating opening 218. In some embodiments, the first valve member 230 can include seals 232 disposed between the first valve member 230 and the valve cavity 214 to isolate the mating opening 218 in a sealed position. During operation, the first valve member 230 can be moved within the valve cavity 214 to be spaced apart from the mating opening 218 and permit flow through the mating opening 218. In some embodiments, the first valve member 230 can be moved toward the end portion 212 of the first connector portion 210 to allow flow through the mating opening 218. Optionally, the valve cavity 214 can have a generally cylindrical volume and allow flow radially outward into the mating opening 218. In some embodiments, the first valve member 230 includes a biasing member 234 to urge the first valve member 230 toward the occluding position. As illustrated, mating of the first connector portion 210 with the second connector portion 240 can displace the first valve member 230 to a flow position and allow flow through the mating opening 218.

In the depicted example, the second valve member 260 is movable within a valve cavity 244 to permit flow through the mating opening 248 and to prevent flow through the mating opening 248. In an occluding position, the second valve member 260 can block, occlude, or seal against the mating opening 248 to prevent flow through the mating opening 248. During operation, the second valve member 260 can be moved within the valve cavity 244 to be spaced apart from the mating opening 248 and permit flow through the mating opening 248. In some embodiments, the second valve member 260 can be moved toward the end portion 242 of the second connector portion 240 to allow flow through the mating opening 248. Optionally, the valve cavity 244 can have a generally annular volume and allow flow radially inward into the mating opening 248. In some embodiments, the second valve member 260 includes a biasing member 264 to urge the second valve member 260 toward the occluding position. As illustrated, mating of the first connector portion 210 with the second connector portion 240 can displace the second valve member 260 to a flow position and allow flow through the mating opening 248.

In the depicted example, the first connector portion 210 and the second connector portion 240 can be engaged to secure or retain the first connector portion 210 and the second connector portion 240 together. As illustrated, the first connector portion 210 and the second connector portion 240 can be coupled together by securing a portion of the first connector portion 210 around the second connector portion 240. In the depicted example, the first connector portion 210 includes or defines one or more engagement fingers 220. As illustrated, the engagement fingers 220 extends axially away from the end portion 212 of the first connector portion 210. Optionally, the engagement fingers 220 can be disposed circumferentially around the flow path 216b and/or the mating opening 218 of the first connector portion 210. In some embodiments, the engagement fingers 220 can each define a ridge or lip 222 that extends radially inward toward the flow path 216b and/or the mating opening 218. Similarly, the second connector portion 240 defines a ridge 252. Optionally, the ridge 252 can be disposed circumferentially around the flow path 246 and/or the mating opening 248 of the second connector portion 240. During operation, the engagement fingers 220 of the first connector portion 210 can engage with the ridge 252 of the second connector portion 240 to couple the first connector portion 210 and the second connector portion 240. In some embodiments, the lip 222 of the engagement fingers 220 can engage with the ridge 252 of the second connector portion 240.

In the depicted example, the engagement fingers 220 and/or the lip 222 of the first connector portion 210 engages the ridge 252 of the second connector portion 240 to resist movement of the first connector portion 210 and the second connector portion 240 in a direction away from each other. Engagement of the engagement fingers 220 against the ridge 252 can, in some instances of the present disclosure, define a snap fitting or snap joint between the first connector portion 210 and the second connector portion 240. In some embodiments, the engagement fingers 220 can deflect to facilitate engagement or disengagement of the engagement fingers 220 with the ridge 252.

Although the engagement fingers 220 are configured to resist separation of the first connector portion 210 and the second connector portion 240, the engagement fingers 220 and/or ridge 252 are also configured to permit separation of the first connector portion 210 and the second connector portion 240 when a threshold force exceeded between the first connector portion 210 and the second connector portion 240. In some embodiments of the present disclosure, the threshold force for separating the first connector portion 210 and the second connector portion 240 is greater than or equal to approximately five pounds (22.25 Newtons). Separation of the first connector portion 210 and the second connector portion 240 can occur when the engagement fingers 220 of the first connector portion 210 are biased or flexed in a direction away from the ridge 252. In the depicted example, the first connector portion 210 and the second connector portion 240 can separate from each other while maintaining the ability to reconnect the first connector portion 210 and the second connector portion 240 together. In some embodiments, the resistance or force to assembly and separation between the first connector portion 210 and the second connector portion 240 can be configured so that the force required for assembly of the first connector portion 210 and the second connector portion 240 is less than the force required for separation the first connector portion 210 and the second connector portion 240.

During operation, the connector 200 can prevent the unintended disconnection of the first connector portion 210 and the second connector portion 240, during certain applications, such as high pressure fluid infusions. In the depicted example, the connector 200 can direct fluid flow to utilize hydraulic force to selectively prevent the disengagement of the engagement fingers 220 of the first connector portion 210 from the ridge 252 of the second connector portion 240.

In the depicted example, the first connector portion 210 can direct fluid flow along the flow path 216a,216b to create or exert an outward radial force to retain the second connector portion 240 relative to the first connector portion 210. As illustrated, the flow path 216b can include one or more turns to exert an outward radial or normal force (or normal force component) on the first connector portion 210 and the second connector portion 240. In some embodiments, the flow path 216b can include a turn to direct flow into the mating opening 218 of the first connector portion 210. Optionally, the mating opening 218 can be disposed substantially perpendicular to a portion of the flow path 216b to allow a turn to direct flow into the mating opening 218 to be substantially perpendicular. As illustrated, the mating opening 218 can be axially aligned with engagement features of the connector 200, such as the engagement fingers 220 of the first connector portion 210 and the ridge 252 of the second connector portion 240. Therefore, in some embodiments, a turn in the flow path 216b to direct flow into the mating opening 218 can create or exert a retaining force that is normal or orthogonal (or otherwise transverse) to the engagement fingers 220 of the first connector portion 210 and/or the ridge 252 of the second connector portion 240.

In the depicted example, the fluid flow through the flow path 216a, 216b of the first connector portion 210 can create or exert an outward radial, normal, or orthogonal force on the body of the first connector portion 210. As illustrated, the fluid flow can create an outward force on the body of the first connector portion 210 that surrounds the annular flow path 216b. In some embodiments, the outward force on the body of the first connector portion 210 can deflect the body radially or outward. Optionally, when the first connector portion 210 and the second connector portion 240 are coupled or mated, the outward force on the body of the first connector portion 210 can deflect the ridge 252 of the second connector portion 240 toward the engagement fingers 220 of the first connector portion 210 to secure or lock engagement between the first connector portion 210 and the second connector portion 240.

In some embodiments, a housing covering 250 can be aligned with the engagement fingers 220 to selectively prevent the radial or outward deflection of the engagement fingers 220. During operation, the engagement fingers 220 and the ridge 252 can be captured between the housing covering 250 and the body of the first connector portion 210, as the engagement fingers 220 and the ridge 252 are urged radially outward by the body of the first connector portion 210 toward the housing covering 250, thereby preventing the disengagement of the engagement fingers 220 from the ridge 252 of the second connector portion 240. In some embodiments, the housing cover 250 can allow for the radial or outward deflection of the engagement fingers 220 when fluid pressure does not sufficiently urge the body of the first connector portion 210 radially outward, permitting the disengagement of the engagement fingers 220 from the ridge 252 of the second connector portion 240. In some embodiments, the housing covering 250 may be rotationally decoupled from the second connector portion 240 and allowed to rotate freely relative to the second connector portion 240.

As described herein, the fluid flow, and the resulting fluid pressure, through the first connector portion 210 can prevent unintentional disengagement of the first connector portion 210 and the second connector portion 240. In some embodiments, the connector 200 can prevent unintentional separation of the first connector portion 210 and the second connector portion 240 due to high separation force caused by high fluid pressures. Advantageously, as fluid pressure through the connector 200 increases, retention force between the first connector portion 210 and the second connector portion 240 similarly increases. In some embodiments, the retention force between the first connector 210 and the second connector portion 240 increases proportionally with the fluid pressure. In some embodiments, the connector 200 can be configured to remain coupled or engaged during high pressure or power injections (of approximately or in excess of 325 psi). Further, the connector 200 can be configured to remain coupled or engaged while experiencing external separation forces (e.g., unintentional pulling of the connector) in response to the fluid pressure through the connector 200. In some embodiments, the amount of external separation force the connector 200 can resist can be in proportion to the fluid pressure through the connector 200.

Figure 5:
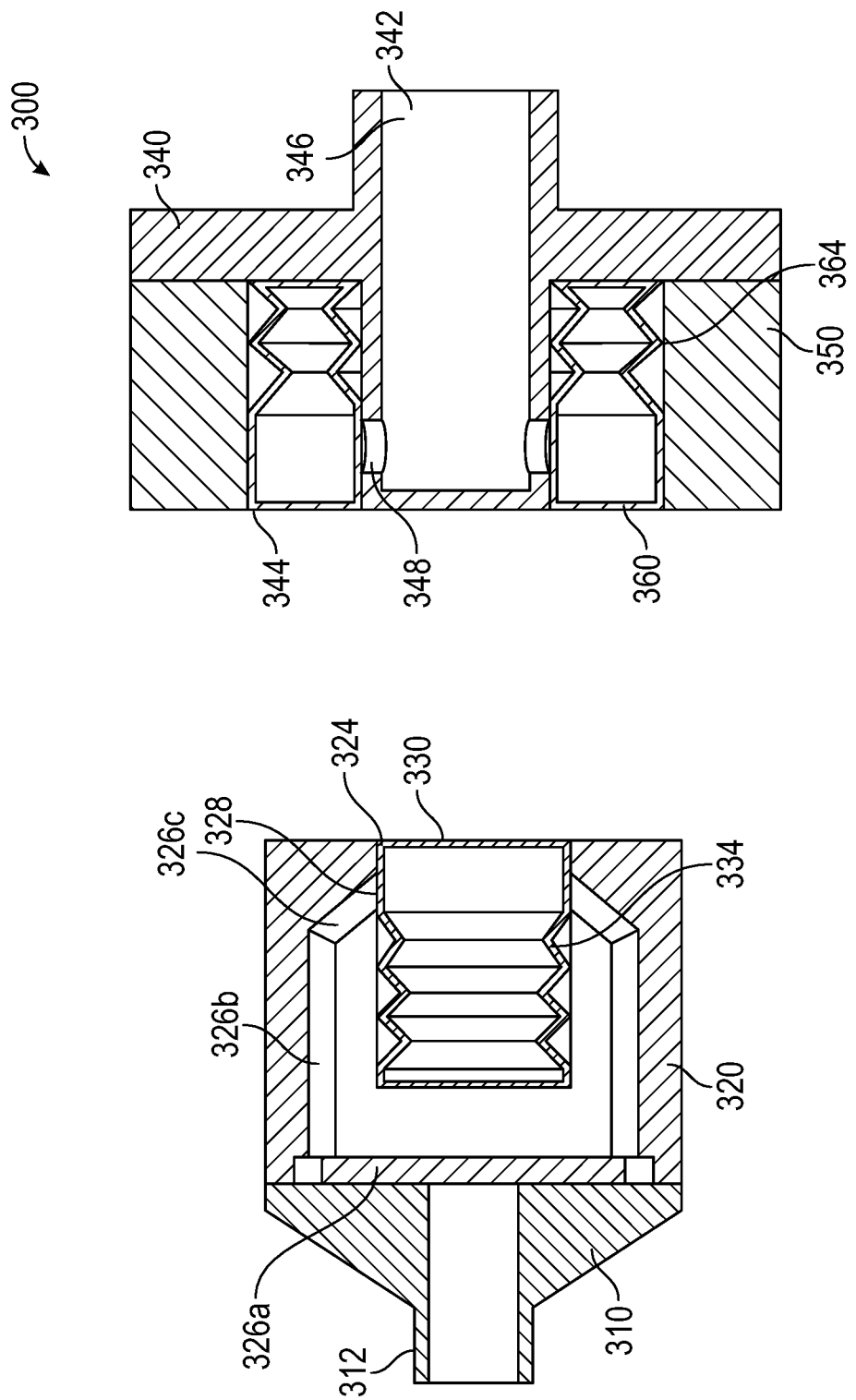
FIG. 5 illustrates a cross-sectional view of a separated fluid connector, in accordance with aspects of the present disclosure.
Figure 6:
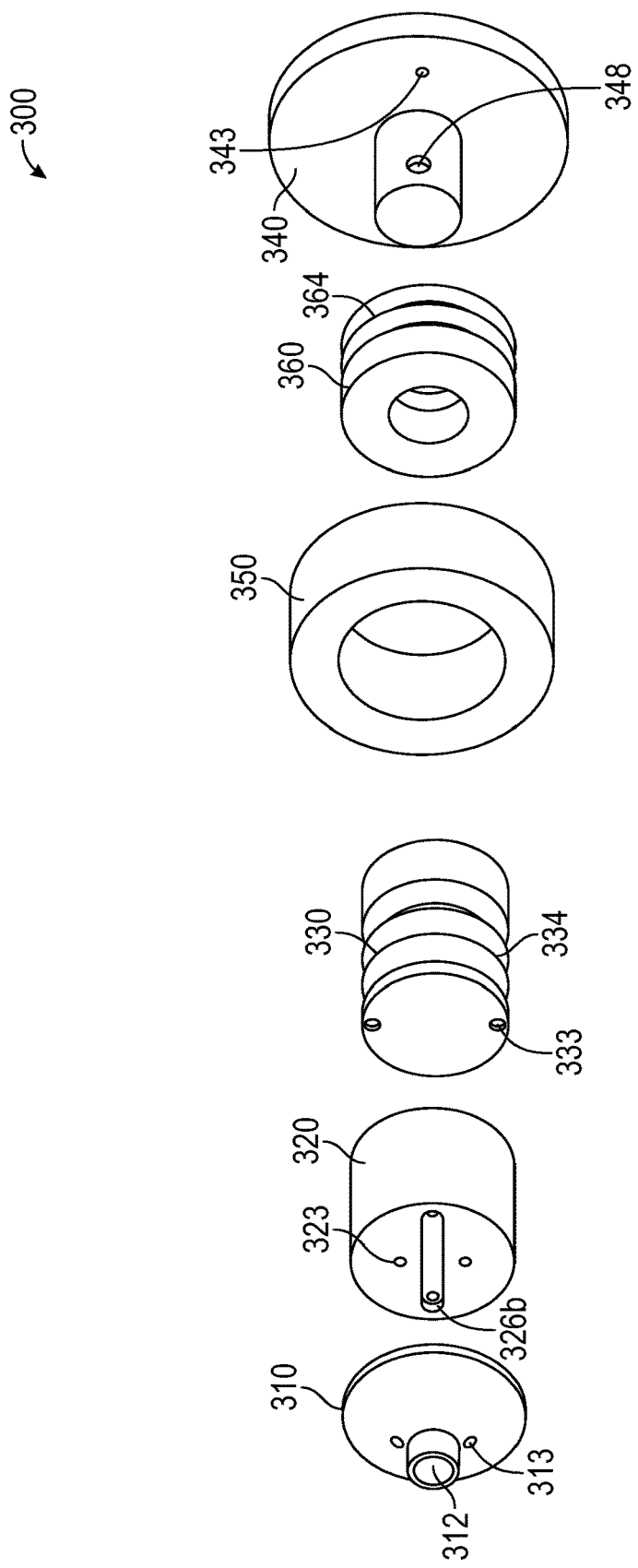
FIG. 6 illustrates an exploded view of a fluid connector of FIG. 5, in accordance with aspects of the present disclosure.
Figure 7:
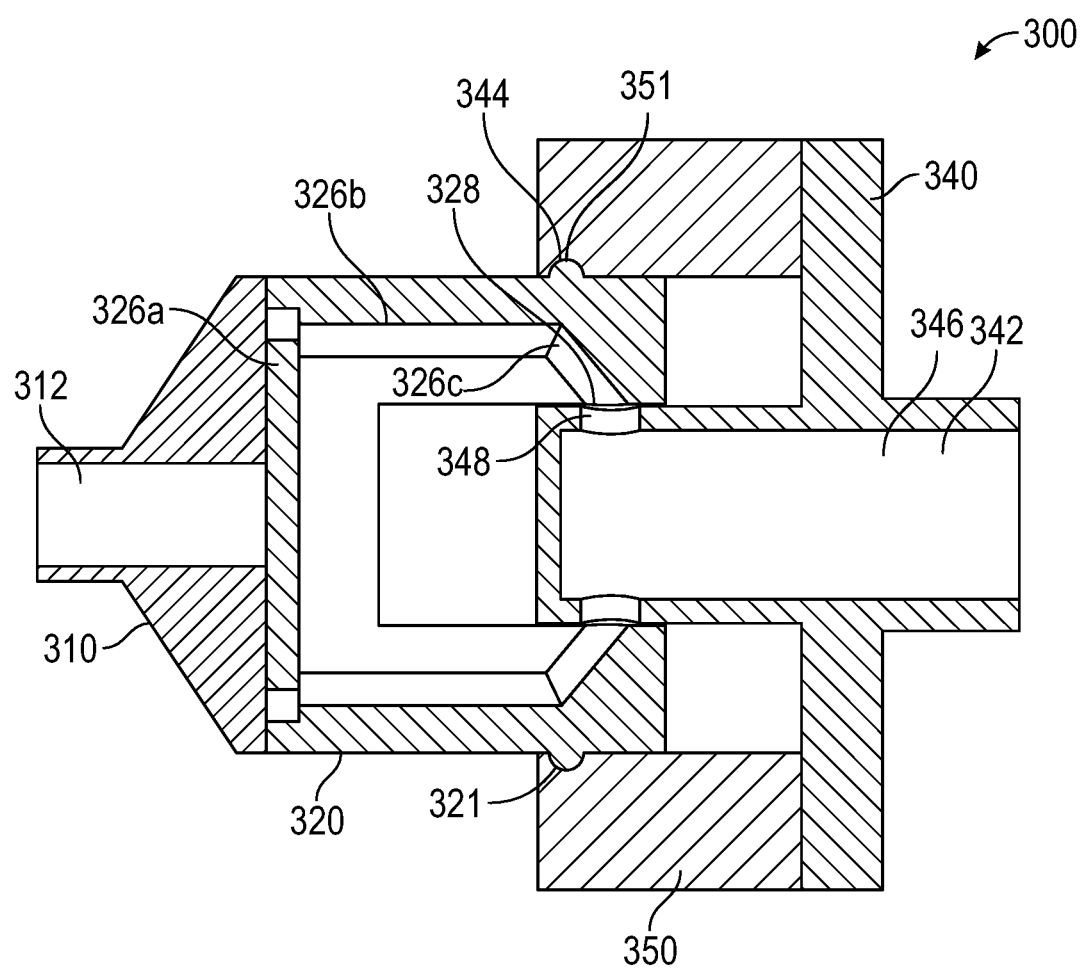
FIG. 7 illustrates a cross-sectional view of a connected fluid connector of FIG. 5, in accordance with aspects of the present disclosure.

FIG. 5 illustrates a cross-sectional view of a separated fluid connector 300, in accordance with aspects of the present disclosure. FIG. 6 illustrates an exploded view of a fluid connector 300 of FIG. 5, in accordance with aspects of the present disclosure. FIG. 7 illustrates a cross-sectional view of a connected fluid connector 300 of FIG. 5, in accordance with aspects of the present disclosure. With reference to FIGS. 5-7, the fluid connector 300 similarly provides a fluid pathway to a patient while allowing for selectable a "fusible link" or quick disconnect, allowing for a controlled disconnection of the fluid connector 300 if excess force is applied and allowing for a maintained connection during high pressure infusions or other procedures.

As illustrated, the fluid connector 300 provides a flow path or fluid pathway from one end of the fluid connector 300 to the opposite end of the fluid connector 300. As illustrated, the fluid connector 300 includes a first connector portion 320 and a second connector portion 340 that are coupled together to form a fluid pathway.

In the depicted example, the first connector portion 320 permits fluid flow to and from the patient or any other portion of the IV set. In the depicted example, the first connector portion 320 includes a tubing portion 310 that defines a bond pocket or end portion 312 to be connected to mating tubing or luer connector. In some embodiments, tubing can be adhered to the tubing portion 310 at the bond pocket or end portion 312. As illustrated, tubing portion 310 can be in fluid communication with the flow path 326a. In some embodiments, the flow path 326a can be in fluid communication with one or more flow paths 326b defined in the body of the first connector portion 320. Therefore, fluid can pass to and from the fluid connector 300 through the mating luer connector via the tubing portion 310 and the flow path 326a, 326b defined in the first connector portion 320.

Further, the second connector portion 340 permits fluid flow to and from a fluid source or any other portion of the IV set. In the depicted example, the second connector portion 340 can be connected to a fluid source or other portion of the IV set. In the depicted example, the second connector portion 340 includes a bond pocket or end portion 342 to be connected to mating tubing or luer connector. In some embodiments, tubing can be adhered to the second connector portion 340 at the bond pocket or end portion 342. As illustrated, a mating tubing or luer connector can be in fluid communication with the flow path 346. Fluid can pass to and from the fluid connector 300 through the second mating luer connector via the flow path 346 defined in the second connector portion 340.

During operation, the first connector portion 320 and the second connector portion 340 can be coupled together to permit flow between the first connector portion 320 and the second connector portion 340. In the depicted example, the first connector portion 320 can define one or more mating openings 328 in fluid communication with the one or more flow paths 326b. As described herein, the flow paths 326b can be in fluid communication with the flow path 326a to allow fluid communication with the tubing or other IV set component coupled to the end portion 312 of the tubing portion 310. Similarly, the second connector portion 340 can define a mating opening 348 in fluid communication with the flow path 346, and the tubing or other IV set component coupled to the end portion 342 of the second connector portion 340. As the first connector portion 320 and the second connector portion 340 are coupled together, fluid can flow between the mating openings 328 of the first connector portion 320 and the mating opening 348 of the second connector portion 340, allowing flow between the first connector portion 320 and the second connector portion 340.

In the depicted example, the first connector portion 320 and the second connector portion 340 each include a septum 330, 360 respectively to control flow through the connector 300. In particular, the septa 330, 360 allow for fluid to flow between the first connector portion 320 and the second connector portion 340 when the first connector portion 320 and the second connector portion 340 are connected and prevent fluid flow when the first connector portion 320 and the second connector portion 340 are disconnected. In some embodiments, the septa 330, 360 can be formed from silicone.

In the depicted example, the first septum 330 is movable within a septum cavity 324 to permit flow through the mating opening 328 and to prevent flow through the mating opening 328. In an occluding position, the first septum 330 can block, occlude, or seal against the mating opening 328 to prevent flow through the mating opening 328. During operation, the first septum 330 can be moved within the septum cavity 324 to be spaced apart from the mating opening 328 and permit flow through the mating opening 328. In some embodiments, the first septum 330 can be moved toward the tubing portion 310 to allow flow through the mating opening 328. Optionally, the septum cavity 324 can have a generally cylindrical volume and allow flow radially outward into the mating opening 328. In some embodiments, the first septum 330 includes a pleated or bellows portion 334 to urge the first septum 330 toward the occluding position. As illustrated, mating of the first connector portion 320 with the second connector portion 340 can displace the first septum 330 to a flow position and allow flow through the mating opening 328. In some embodiments, the first septum 330 can include one or more air channels 333 to allow for the expansion and contraction of the bellows portion 334 and/or the first septum 330 generally as the first septum 330 is moved between the occluding position and the flow position. The air channels 333 of the first septum 330 can be in fluid communication with the environment via air channels 323, 313 disposed in the first connector portion 320 and the tubing portion 310, respectively.

In the depicted example, the second septum 360 is movable within a valve cavity 344 to permit flow through the mating opening 348 and to prevent flow through the mating opening 348. In an occluding position, the second septum 360 can block, occlude, or seal against the mating opening 348 to prevent flow through the mating opening 348. During operation, the second septum 360 can be moved within the valve cavity 344 to be spaced apart from the mating opening 348 and permit flow through the mating opening 348. In some embodiments, the second septum 360 can be moved toward the end portion 342 of the second connector portion 340 to allow flow through the mating opening 348. Optionally, the valve cavity 344 can have a generally annular volume and allow flow radially inward into the mating opening 348. In some embodiments, the second septum 360 includes a pleated or bellows portion 364 to urge the second septum 360 toward the occluding position. As illustrated, mating of the first connector portion 320 with the second connector portion 340 can displace the second septum 360 to a flow position and allow flow through the mating opening 348. In some embodiments, the second septum 360 can include one or more air channels to allow for the expansion and contraction of the bellows portion 364 and/or the second septum 360 generally as the second septum 360 is moved between the occluding position and the flow position. The air channels of the second septum 360 can be in fluid communication with the environment via air channels 343 disposed in the second connector portion 340.

In the depicted example, the first connector portion 320 and the second connector portion 340 can be engaged to secure or retain the first connector portion 320 and the second connector portion 340 together. As illustrated, the first connector portion 320 and the second connector portion 340 can be coupled together by securing a portion of the first connector portion 320 within the second connector portion 340. In the depicted example, the first connector portion 320 includes or defines one or more snap fittings 321. As illustrated, the snap fittings 321 extend radially away from the body of the first connector portion 320. Optionally, the snap fittings 321 can be disposed circumferentially around the flow path 326b and/or the mating opening 328 of the first connector portion 320. Further, as illustrated, the second connector portion 340 can include an engagement ring 350 to receive a portion of the first connector portion 320. The engagement ring 350 can define a groove 351. Optionally, the groove 351 can be disposed circumferentially around the flow path 346 and/or the mating opening 348 of the second connector portion 340. During operation, the snap fittings 321 of the first connector portion 320 can engage with the groove 351 of the engagement ring 350 to couple the first connector portion 320 and the second connector portion 340.

In the depicted example, the snap fittings 321 of the first connector portion 320 engages the groove 351 of the engagement ring 350 to resist movement of the first connector portion 320 and the second connector portion 340 in a direction away from each other. In some embodiments, the snap fittings 321 or the groove 351 can deflect to facilitate engagement or disengagement of the snap fittings 321 with the groove 351.

Although the snap fittings 321 and the groove 351 are configured to resist separation of the first connector portion 320 and the second connector portion 340, the snap fittings 321 and/or groove 351 are also configured to permit separation of the first connector portion 320 and the second connector portion 340 when a threshold force exceeded between the first connector portion 320 and the second connector portion 340. In some embodiments of the present disclosure, the threshold force for separating the first connector portion 320 and the second connector portion 340 is greater than or equal to approximately five pounds (22.25 Newtons). Separation of the first connector portion 320 and the second connector portion 340 can occur when the snap fittings 321 of the first connector portion 320 are biased or flexed out of engagement with the groove 351. In the depicted example, the first connector portion 320 and the second connector portion 340 can separate from each other while maintaining the ability to reconnect the first connector portion 320 and the second connector portion 340 together. In some embodiments, the resistance or force to assembly and separation between the first connector portion 320 and the second connector portion 340 can be configured so that the force required for assembly of the first connector portion 320 and the second connector portion 340 is less than the force required for separation the first connector portion 320 and the second connector portion 340.

During operation, the connector 300 can prevent the unintended disconnection of the first connector portion 320 and the second connector portion 340, during certain applications, such as high pressure fluid infusions. In the depicted example, the connector 300 can direct fluid flow to utilize hydraulic force to selectively prevent the disengagement of the snap fittings 321 of the first connector portion 320 from the groove 351 of the second connector portion 340.

In the depicted example, the first connector portion 320 can direct fluid flow along the flow path 326a,326b to create or exert an outward radial force to retain the second connector portion 340 relative to the first connector portion 320. As illustrated, the flow path 326b can define one or more turns or angled portions to exert an outward radial or normal force component on the first connector portion 320 and the second connector portion 340. In some embodiments, the flow path 326b can include an angled portion 326c to direct flow into the mating opening 328 of the first connector portion 320. Optionally, the mating opening 328 can be disposed substantially perpendicular to a portion of the flow path 326b to allow the angled portion 326c to direct flow into the mating opening 328 to include a perpendicular component. As illustrated, the mating opening 328 can be axially aligned with engagement features of the connector 300, such as the snap fittings 321 of the first connector portion 320 and the groove 351 of the engagement ring 350. Therefore, in some embodiments, an angled portion 326c in the flow path to direct flow into the mating opening 328 can create or exert a retaining force that includes a normal or orthogonal component to the snap fittings 321 of the first connector portion 320 and/or the groove 351 of the engagement ring 350.

In the depicted example, the fluid flow through the flow path 326b and/or the angled portion 326c of the first connector portion 320 can create or exert an outward radial, normal, or orthogonal force component on the body of the first connector portion 320. As illustrated, the fluid flow can create an outward force on the body of the first connector portion 320 that surrounds the flow path 326b and the angled portion 326c. In some embodiments, the outward force on the body of the first connector portion 320 can deflect the body radially or outward. Optionally, when the first connector portion 320 and the second connector portion 340 are coupled or mated, the outward force on the body of the first connector portion 320 can deflect the snap fittings 321 of the first connector portion 320 toward the groove 351 or engagement ring 350 of the second connector portion 340 to secure or lock engagement between the first connector portion 320 and the second connector portion 340.

As described herein, the fluid flow, and the resulting fluid pressure, through the first connector portion 320 can prevent unintentional disengagement of the first connector portion 320 and the second connector portion 340. In some embodiments, the connector 300 can prevent unintentional separation of the first connector portion 320 and the second connector portion 340 due to high separation force caused by high fluid pressures. Advantageously, the connector 300 can isolate forces and allow for neutral flow, such that as fluid pressure through the connector 300 increases, retention force between the first connector portion 320 and the second connector portion 340 similarly increases. In some embodiments, the retention force between the first connector portion 320 and the second connector portion 340 increases proportionally with the fluid pressure. In some embodiments, the connector 300 can be configured to remain coupled or engaged during high pressure or power injections (of approximately or in excess of 325 psi). Further, the connector 300 can be configured to remain coupled or engaged while experiencing external separation forces (e.g., unintentional pulling of the connector) in response to the fluid pressure through the connector 300. In some embodiments, the amount of external separation force the connector 300 can resist can be in proportion to the fluid pressure through the connector 300.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A connector comprising: a first connector portion comprising: a connector housing comprising: a connector body defining a tubing opening and a mating opening, wherein the connector body defines a flow path between the tubing opening and the mating opening; and an engagement portion at least partially surrounding the connector body, the engagement portion defining an engagement lip extending radially toward the connector body, wherein the engagement lip is configured to releasably engage the connector housing with a mating connector portion, wherein the flow path comprises at least one portion that is normal to the engagement portion, wherein fluid flow through the flow path exerts a normal force on the connector housing and prevent release of the connector housing with the mating connector portion.

Clause 2. The connector of Clause 1, wherein the flow path defines at least one turn.

Clause 3. The connector of Clause 1, wherein the mating opening is disposed perpendicular to a portion of the flow path.

Clause 4. The connector of Clause 1, wherein the flow path comprises a central portion adjacent to the tubing opening.

Clause 5. The connector of Clause 1, wherein the flow path comprises an annular portion adjacent to the mating opening.

Clause 6. The connector of Clause 5, wherein fluid flow from the annular portion of the flow path to the mating opening exerts the normal force on the connector housing.

Clause 7. The connector of Clause 1, wherein the flow path comprises an angled portion adjacent to the mating opening.

Clause 8. The connector of Clause 7, wherein fluid flow from the angled portion of the flow path to the mating opening exerts the normal force on the connector housing.

Clause 9. The connector of Clause 1, wherein the first connector portion further comprises: a movable seal configured to selectively prevent fluid flow through the mating opening and to move and permit fluid flow through the mating opening.

Clause 10. The connector of Clause 9, wherein the movable seal is disposed within a cavity of the connector body.

Clause 11. The connector of Clause 9, wherein the movable seal is urged toward the mating opening by a biasing member.

Clause 12. The connector of Clause 9, wherein the movable seal comprises a bellows.

Clause 13. The connector of Clause 1, further comprising: a second connector portion comprising defining a second tubing opening and a second mating opening, wherein the second connector portion defines a second flow path between the second mating opening and the tubing opening, wherein the mating opening of the first connector portion and the second mating opening of the second connector portion are in fluid communication when the first connector portion and the second connector portion are in engagement, the first connector portion and the second connector portion are configured to be in separable engagement when fluid flow through the flow path is below a critical rate and to be in locking engagement when fluid flow through the flow path is above a critical rate.

Clause 14. The connector of Clause 13, wherein fluid flow through the second flow path exerts a normal force on the connector housing and the second connector portion and prevents release of the first connector portion from the second connector portion.

Clause 15. The connector of Clause 13, wherein the second connector portion extends into a cavity of the connector body of the first connector portion.

Clause 16. The connector of Clause 13, wherein the second connector portion further comprises: a second movable seal configured to selectively prevent fluid flow through the second mating opening and to move and permit fluid flow through the second mating opening.

Clause 17. The connector of Clause 13, wherein the second connector portion further comprises: a second engagement portion defining a second engagement lip extending radially away from the second connector portion, wherein the second engagement lip is configured to releasably engage the engagement lip of the first connector portion.

Clause 18. A connector comprising: a first connector portion defining a tubing opening and a mating opening, wherein the first connector portion defines a flow path between the tubing opening and the mating opening; and a second connector portion comprising defining a second tubing opening and a second mating opening, wherein the second connector portion defines a second flow path between the second mating opening and the tubing opening, wherein the mating opening of the first connector portion and the second mating opening of the second connector portion are in fluid communication when the first connector portion and the second connector portion are in engagement, wherein the flow path or the second flow path comprises at least one portion that is normal to an overlapping portion of the first connector portion and the second connector portion, wherein fluid flow through the flow path or the second flow path exerts a normal force on the overlapping portion of the first connector portion and the second connector portion and prevent release of the first connector portion with the second connector portion.

Clause 19. The connector of Clause 18, wherein the first connector portion and the second connector portion are configured to be in separable engagement when fluid flow through the flow path or the second flow path is below a critical rate and to be in locking engagement when fluid flow through the flow path or the second flow path is above a critical rate.

Clause 20. The connector of Clause 18, wherein the first connector portion comprises: a movable seal configured to selectively prevent fluid flow through the mating opening and to move and permit fluid flow through the mating opening; and wherein the second connector portion comprises: a second movable seal configured to selectively prevent fluid flow through the second mating opening and to move and permit fluid flow through the second mating opening.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A connector comprising:
    a first connector portion comprising:
        a connector housing comprising:
            a connector body defining a tubing opening and a mating opening, wherein the connector body defines a flow path between the tubing opening and the mating opening; and
            an engagement portion at least partially surrounding the connector body, the engagement portion defining an engagement lip extending radially toward the connector body, wherein the engagement lip is configured to releasably engage the connector housing with a second connector portion of the connector,
        wherein the flow path comprises at least one portion that is normal to the engagement portion, wherein fluid flow through the flow path exerts a normal force on the connector housing and prevent release of the connector housing with the second connector portion of the connector.

2. The connector of claim 1, wherein the flow path defines at least one turn.

3. The connector of claim 1, wherein the mating opening is disposed perpendicular to a portion of the flow path.

4. The connector of claim 1, wherein the flow path comprises a central portion adjacent to the tubing opening.

5. The connector of claim 1, wherein the flow path comprises an annular portion adjacent to the mating opening.

6. The connector of claim 5, wherein fluid flow from the annular portion of the flow path to the mating opening exerts the normal force on the connector housing.

7. The connector of claim 1, wherein the flow path comprises an angled portion adjacent to the mating opening.

8. The connector of claim 7, wherein fluid flow from the angled portion of the flow path to the mating opening exerts the normal force on the connector housing.

9. The connector of claim 1, wherein the first connector portion further comprises:
    a movable seal configured to selectively prevent fluid flow through the mating opening and to move and permit fluid flow through the mating opening.

10. The connector of claim 9, wherein the movable seal is disposed within a cavity of the connector body.

11. The connector of claim 9, wherein the movable seal is urged toward the mating opening by a biasing member.

12. The connector of claim 9, wherein the movable seal comprises a bellows.

13. The connector of claim 1, wherein
the second connector portion comprises a second tubing opening and a second mating opening, wherein the second connector portion defines a second flow path between the second mating opening and the second tubing opening, wherein the mating opening of the first connector portion and the second mating opening of the second connector portion are in fluid communication when the first connector portion and the second connector portion are in engagement, the first connector portion and the second connector portion are configured to be in separable engagement when fluid flow through the flow path is below a critical rate and to be in locking engagement when fluid flow through the flow path is above the critical rate.

14. The connector of claim 13, wherein fluid flow through the second flow path exerts a normal force on the connector housing and the second connector portion and prevents release of the first connector portion from the second connector portion.

15. The connector of claim 13, wherein the second connector portion extends into a cavity of the connector body of the first connector portion.

16. The connector of claim 13, wherein the second connector portion further comprises:
a second movable seal configured to selectively prevent fluid flow through the second mating opening and to move and permit fluid flow through the second mating opening.

17. The connector of claim 13, wherein the second connector portion further comprises:
a second engagement portion defining a second engagement lip extending radially away from the second connector portion, wherein the second engagement lip is configured to releasably engage the engagement lip of the first connector portion.

18. A connector comprising:
a first connector portion defining a tubing opening and a mating opening, wherein the first connector portion defines a flow path between the tubing opening and the mating opening; and
a second connector portion comprising a second tubing opening and a second mating opening, wherein the second connector portion defines a second flow path between the second mating opening and the second tubing opening, wherein the mating opening of the first connector portion and the second mating opening of the second connector portion are in fluid communication when the first connector portion and the second connector portion are in engagement,
wherein the flow path or the second flow path comprises at least one portion that is normal to an overlapping portion of the first connector portion and the second connector portion, wherein fluid flow through the flow path or the second flow path exerts a normal force on the overlapping portion of the first connector portion and the second connector portion and prevent release of the first connector portion with the second connector portion.

19. The connector of claim 18, wherein the first connector portion and the second connector portion are configured to be in separable engagement when fluid flow through the flow path or the second flow path is below a critical rate and to be in locking engagement when fluid flow through the flow path or the second flow path is above the critical rate.

20. The connector of claim 18, wherein the first connector portion comprises:
a movable seal configured to selectively prevent fluid flow through the mating opening and to move and permit fluid flow through the mating opening; and
wherein the second connector portion comprises:
a second movable seal configured to selectively prevent fluid flow through the second mating opening and to move and permit fluid flow through the second mating opening.

* * * * *